United States Patent [19]

Leibinsohn

[11] Patent Number: 4,627,554

[45] Date of Patent: Dec. 9, 1986

[54] DEVICE FOR DISPENSING A LIQUID FROM A COLLAPSIBLE CONTAINER

[76] Inventor: Saul Leibinsohn, 11 Olei Hagardom Street, Rishon Lezion, Israel

[21] Appl. No.: 694,250

[22] Filed: Jan. 24, 1985

[51] Int. Cl.$^4$ ............................................. B65D 35/28
[52] U.S. Cl. ...................... 222/103; 224/148
[58] Field of Search .................. 222/95, 92, 107, 106, 222/103, 175; 224/148, 202, 235, 237; 604/212, 214; 383/906, 66

[56] References Cited

U.S. PATENT DOCUMENTS

| | | | |
|---|---|---|---|
| 2,500,846 | 3/1950 | McFarland | 224/202 |
| 2,644,623 | 7/1953 | White | 224/148 |
| 2,915,222 | 12/1959 | Purinton | 222/103 |
| 3,960,294 | 6/1976 | Bernard | 222/103 |
| 4,420,097 | 12/1983 | Motsenbocker | 222/175 |

FOREIGN PATENT DOCUMENTS 2509962 3/1975 Fed. Rep. of Germany ...... 222/103

Primary Examiner—H. Grant Skaggs
Assistant Examiner—Kenneth Noland
Attorney, Agent, or Firm—Benjamin J. Barish

[57] ABSTRACT

A device for dispensing a liquid from a collapsible container comprises a pair of elastic plates hingedly mounted to each other along one edge permitting them to be pivoted to an open position or to a closed position, and a sleeve of flexible material secured to the pair of elastic plates along their hinged edges for receiving a liquid-filled collapsible container. Each of the elastic plates is pre-formed with a curve which is convex from the side facing the flexible sleeve. The arrangement is such that when the liquid-filled collapsible container is received within the flexible sleeve and the two curved elastic plates are pivoted to their closed positions, they apply, due to their elasticity, a continuous force to the collapsible container for dispensing the liquid therefrom. The device further includes retainer devices for releasably retaining the elastic plates in their closed position.

17 Claims, 3 Drawing Figures

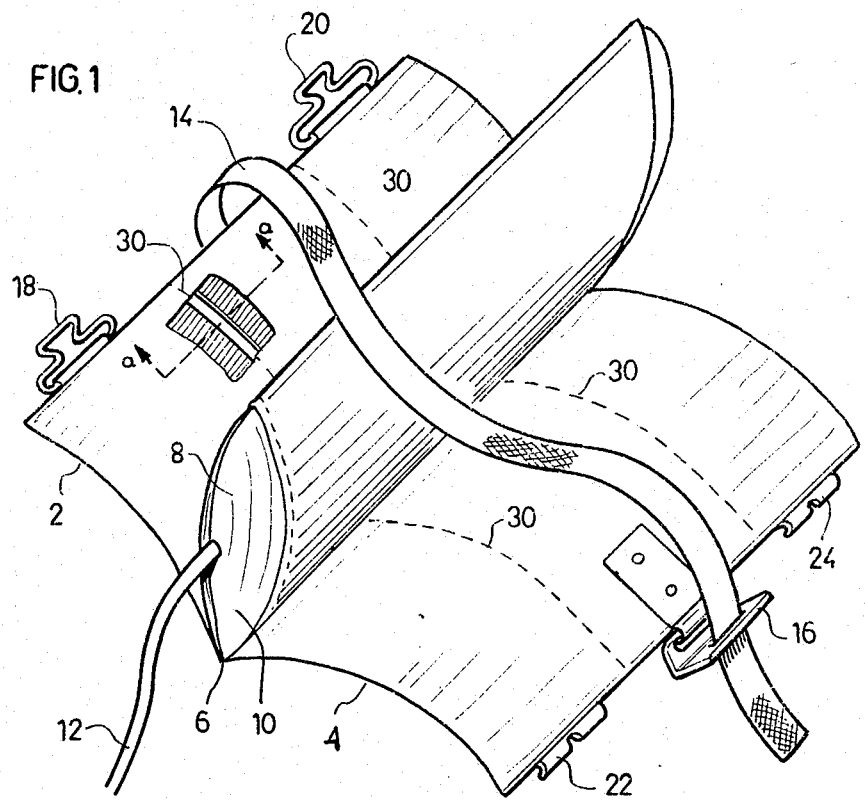
FIG. 1
FIG. 1a
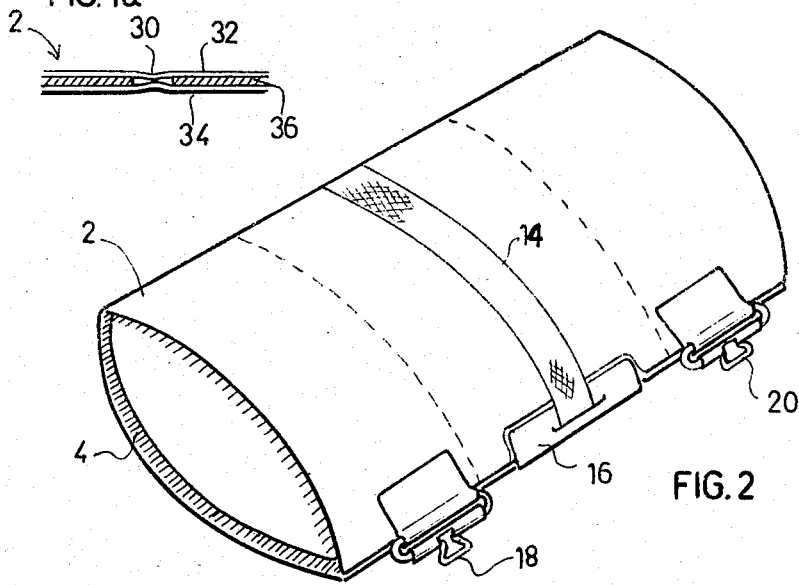
FIG. 2

DEVICE FOR DISPENSING A LIQUID FROM A COLLAPSIBLE CONTAINER

BACKGROUND OF THE INVENTION

The present invention relates to a device for dispensing a liquid from a collapsible container. The invention is particularly useful for dispensing infusion liquids, and is therefore described below with respect to this application, but it will be appreciated that the invention could advantageously be used in other applications as well.

Infusion devices, as commonly used in the medical field, frequently require that the infusion liquid be dispensed at a substantially constant pressure. One of the disadvantages of many known types of such devices, particularly the simpler ones, is that the infusion pressure does not remain substantially constant, but rather changes with the change in volume of the infusion bag occurring during the infusion operation. The known infusion assemblies, wherein such a substantially constant pressure is maintained, are generally of relatively complicated construction and therefore costly to produce.

SUMMARY OF THE INVENTION

An object of the present invention is to provide a device of simple construction for dispensing a liquid from a collapsible container. Another object of the invention is to provide a device particularly useful for dispensing an infusion liquid at a substantially constant pressure throughout the infusion operation.

According to a broad aspect of the present invention, there is provided a device for dispensing a liquid from a collapsible container, comprising: a pair of elastic plates hingedly mounted to each other along one edge permitting them to be pivoted to an open position or to a closed position; a sleeve of flexible material secured to the pair of elastic plates along their hinged edges for receiving a liquid-filled collapsible container; each of the pair of elastic plates being pre-formed with a curve which is convex from the side facing the flexible sleeve such that when the liquid-filled collapsible container is received within the flexible sleeve and the two curved elastic plates are pivoted to their closed positions, they apply, due to their elasticity, a continuous force to the collapsible container for dispensing the liquid therefrom; and retainer means for releasably retaining the pair of elastic plates in their closed position.

According to another feature of the present invention, each of the elastic plates is sectioned along parallel lines perpendicular to their hinged edges such as to permit compact foling of the assembly when not in use.

Further features and advantages of the invention will be apparent from the description below.

BRIEF DESCRIPTION OF THE DRAWINGS

The invention is herein described, by way of example only, with reference to the accompanying drawings, wherein:

FIG. 1 is a three-dimensional view illustrating one form of device constructed in accordance with the invention for dispensing a liquid from a collapsible container, the assembly illustrated in FIG. 1 being shown in its open position and being partly sectioned;

FIG. 1a is a fragmentary sectional view along lines a—a of FIG. 1; and

FIG. 2 illustrates the elastic assembly of FIG. 1 in its closed position.

DESCRIPTION OF A PREFERRED EMBODIMENT

The elastic assembly illustrated in the drawings comprises two elastic plates 2,4, hingedly mounted to each other along their inner edges 6 to permit them to pivot to an open position, as shown in FIG. 1, or to a closed position as shown in FIG. 2. The assembly further includes a sleeve 8 of flexible material secured to the two curved elastic plates 4 along their hinged edges 6 for receiving a collapsible container 10 containing the liquid to be dispensed. For example, container 10 may be an infusion bag as used in the medical field and containing an infusion to be dispensed via an outlet tube 12.

Each of the two elastic plates, 2,4 is pre-formed with a curve which is convex from the side facing the sleeve 8 (FIG. 1), and which extends continuously from its hinged edge to its outer edge. The arrangement is such that when the liquid-filled collapsible container 10 is received within the flexible sleeve 8, and the two curved elastic plates are pivoted to their closed position as shown in FIG. 2, they apply, due to their elasticity, a continuous squeezing force to the container 10 for dispensing the liquid therefrom through its outlet tube 10. The two elastic plates are retained in their closed position by retainer means including a strap 14 fixed centrally of the free edge of plate 2 and receivable within a buckle 16 fixed centrally of the free edge of plate 4. These retainer elements further include clasps 18 and 20 fixed to the outer edges of plate 2 on opposite sides of strap 14, and co-operable with clasps 22 and 24 fixed to the outer edge of plage 4 on opposite sides of its buckle 16.

The two elastic plates 2,4 are each pre-formed with a curve which preferably follows the arc of a circle. In the illustrated embodiment, the curve of each elastic plate defines substantially a 90° arc.

As shown particularly in FIGS. 1 and 1a, each of the elastic plates 2,4 is sectioned along parallel lines 30 perpendicular to their hinged edges 6. This is to permit compact folding of the assembly along lines 30 when not in use. To provide this collapsible arrangement, each of the two elastic plates 2,4 comprises an outer flexible covering constituted of two layers of flexible material 32,34 (such as fabric), and a plurality of pre-curved elastic plate section 36 (such as spring steel) in side-by-side relationship but spaced from each along the fold lines 30, thereby permitting the assembly to be folded along these fold lines for compact storage or handling when not in use.

The illustrated device is used in the following manner: First, the device is opened, as shown in FIG. 1, and the collapsible bag 10, containing the liquid (e.g., an infusion liquid) to be dispensed, is inserted within flexible sleeve 8 secured to the hinged edges 6 of the two elastic plates 2,4. The two elastic plates are then closed by passing strap 14 through buckle 16 and pulling on the strap to draw the two elastic plates 2,4 together and to enclose the collapsible bag 10 within sleeve 8 of the assembly. This closing operation stresses the two elastic plates 2,4, deforming them in the direction opposite to their curvatures. The two plates, due to their elasticity, thus apply a compressive force to the collapsible bag 10 within sleeve 8. To apply the maximum force, strap 14 is drawn until the outer edge of elastic plate 2 is brought to the outer edge of elastic plate 4, whereupon the strap is secured within buckle 16. Clasps 18 and 20 at the opposite ends of elastic plate 2 are then pivoted so as to engage clasps 22 and 24 at the opposite ends of elastic plage 4, thereby firmly retaining the assembly in its closed positron with the collapsible container 10 under compressive pressure by the stresses produced in the pre-curved elastic plates 2 and 4.

With the arrangement illustrated in the drawings, the pressure applied to the collapsible container 10 remains substantially constant throughout the dispensing operation, even as the volume of the container decreases with the dispensing of the liquid material therefrom.

When the illustrated assembly is not in use, for example, during storage or handling, it may be folded into a compact form along fold lines 30.

While the invention has been described with respect to dispensing infusion liquids, it will be appreciated that it could also be used in other applications, for example in dispensing fire-extinguisher liquids, creams, or other materials in fluid form. The above-described embodiment of the invention is therefore to be considered purely for purposes of example, it being appreciated that many other variations, modifications, and applications of the invention may be made.

What is claimed is:

1. A device for dispensing a liquid from a collapsible container, comprising: a pair of elastic plates hingedly mounted to each other along one edge permitting them to be pivoted to an open position or to a closed position; a sleeve of flexible material secured to the pair of elastic plates along their hinged edges for receiving a liquid-filled collapsible container; each of said pair of elastic plates being pre-formed with a curve which is convex from the side facing said flexible sleeve such that when the liquid-filled collapsible container is received within said flexible sleeve and the two curved elastic plates are pivoted to their closed positions, they apply, due to their elasticity, a continuous force to the collapsible container for dispensing the liquid therefrom; each of said elastic plates being sectioned along parallel lines perpendicular to their hinged edges such as to permit compact folding of the assembly when not in use; and retainer means for releasably retaining said pair of elastic plates in their closed position.

2. The device according to claim 1, wherein said pair of elastic plates are each pre-formed with a curve substantially following the arc of a circle.

3. The device according to claim 2, wherein said pair of elastic plates are each pre-formed with a curve substantially following a 90° arc of a circle.

4. The device according to claim 1, wherein each of said sectioned elastic plates comprises an outer flexible covering enclosing a plurality of pre-curved elastic plate sections in spaced side-by-side relationship to permit compact folding of the assembly when not in use.

5. The device according to claim 1, wherein each of said elastic plates comprises three sections.

6. The device according to claim 1, wherein each of said elastic plates includes an outer flexible covering.

7. The device according to claim 1, wherein said retainer means includes a strap fixed to the center of the outer edge of one of said elastic plates and receivable in a buckle fixed to the center of the outer edge of the other of said elastic plates for drawing the two elastic plates together when closing the assembly.

8. The device according to claim 7, wherein said retainer means further i,ncludes a clasp at each of the outer ends of one elastic plate co-operable with a clasp at each of the opposite ends of the other of said elastic plates to retain the two elastic plates in their closed positions when drawn together by said strap.

9. The device according to claim 1, further including a liquid-filled collapsible container received within said sleeve of flexible material.

10. A device for dispensing a liquid from a collapsible container, comprising: a pair of elastic plates hingedly mounted to each other along one edge permitting them to be pivoted to an open position or to a closed position; a sleeve of flexible material secured to the pair of elastic plates along their hinged edges for receiving a liquid-filled collapsible container; each of said elastic plates being sectioned along parallel lines perpendicular to their hinged edges such as to permit compact folding of the assembly when not in use; and retainer means for releasably retaining said pair of elastic plates in their closed position.

11. The device according to claim 10, wherein said pair of elastic plates are each pre-formed with a curve substantially following the arc of a circle.

12. The device according to claim 11, wherein said pair of elastic plates are each pre-formed with a curve substantially following a 90° arc of a circle.

13. The device according to claim 10, wherein each of said sectioned elastic plates comprises an outer flexible covering enclosing a plurality of elastic plate sections in spaced side-by-side relationship to permit compact folding of the assembly when not in use.

14. The device according to claim 13, wherein each of said elastic plates comprises three sections.

15. The device according to claim 10, wherein each of said elastic plates includes an outer flexible covering.

16. The device according to claim 10, wherein said retainer means includes a strap fixed to the center of the outer edge of one of said elastic plates and receivable in a buckle fixed to the center of the outer edge of the other of said elastic plates for drawing the two elastic plates together when closing the assembly.

17. The device according to claim 16, wherein said retainer means further includes a clasp at each of the outer ends of one elastic plate co-operable with a clasp at each of the opposite ends of the other of said elastic plates to retain the two elastic plates in their closed positions when drawn together by said strap.

* * * * *